US008625828B2

(12) United States Patent
Flynn et al.

(10) Patent No.: US 8,625,828 B2
(45) Date of Patent: Jan. 7, 2014

(54) HEARING PROSTHESIS HAVING AN ON-BOARD FITTING SYSTEM

(75) Inventors: Mark Flynn, Gothenberg (SE); Kristian Asnes, Molndal (SE); Martin E. G. Hillbratt, Vastra Gotaland (SE); Fredrik Breitholtz, Gothenberg (SE)

(73) Assignee: Cochlear Limited, Macquarie University, NSW (AU)

( * ) Notice: Subject to any disclaimer, the term of this patent is extended or adjusted under 35 U.S.C. 154(b) by 459 days.

(21) Appl. No.: 12/771,529

(22) Filed: Apr. 30, 2010

(65) Prior Publication Data

US 2011/0270014 A1 Nov. 3, 2011

(51) Int. Cl.
*H04R 25/00* (2006.01)
*A61N 1/00* (2006.01)

(52) U.S. Cl.
USPC ................ 381/326; 381/314; 600/25; 607/57

(58) Field of Classification Search
USPC ........................ 381/326, 314; 600/25; 607/57
See application file for complete search history.

(56) References Cited

U.S. PATENT DOCUMENTS 4,498,461 A 2/1985 Hakansson
4,532,930 A * 8/1985 Crosby et al. .................. 607/57
4,904,233 A * 2/1990 Håkansson et al. ............. 600/25
4,953,112 A * 8/1990 Widin et al. ...................... 703/6
5,012,520 A * 4/1991 Steeger ......................... 381/315
5,095,904 A * 3/1992 Seligman et al. ............... 607/57
5,271,397 A * 12/1993 Seligman et al. ............. 607/137
5,277,694 A * 1/1994 Leysieffer et al. .............. 600/25
5,626,629 A * 5/1997 Faltys et al. ...................... 607/57
5,824,022 A * 10/1998 Zilberman et al. .............. 607/57
6,157,861 A * 12/2000 Faltys et al. ...................... 607/57
6,205,360 B1 3/2001 Carter et al.
6,289,247 B1 * 9/2001 Faltys et al. ...................... 607/57
6,537,200 B2 * 3/2003 Leysieffer et al. .............. 600/25
6,565,503 B2 5/2003 Leysieffer et al.
6,575,894 B2 6/2003 Leysieffer et al.
6,697,674 B2 * 2/2004 Leysieffer ........................ 607/57
6,879,860 B2 * 4/2005 Wakefield et al. .............. 607/57
7,074,222 B2 7/2006 Westerkull
7,343,021 B2 * 3/2008 Takagi et al. ................. 381/313

(Continued)

FOREIGN PATENT DOCUMENTS

WO WO 2004/080532 A1 9/2004
WO 2005029915 3/2005
WO 2009/083372 7/2009
WO WO 2009083372 A2 * 7/2009

OTHER PUBLICATIONS

Takagi, H., "Interactive Evolutionary Computation: Fusion of the Capabilities of EC Optimization and Human Evaluation", Proceedings of the IEEE, Sep. 2001, pp. 1275-1296, vol. 89, No. 9.

(Continued)

*Primary Examiner* — David Warren
*Assistant Examiner* — Christina Russell
(74) *Attorney, Agent, or Firm* — Kilpatrick, Townsend & Stockton, LLP.

(57) ABSTRACT

A hearing prosthesis comprising an external component having an integrated user interface, a sound processor configured to process received sounds based on predefined fitting data, and an on-board fitting system configured to set the fitting data in response to control inputs received via the integrated user interface.

20 Claims, 16 Drawing Sheets

(56) References Cited

U.S. PATENT DOCUMENTS

| | | | | |
|---|---|---|---|---|
| 7,664,279 | B2 * | 2/2010 | Flynn et al. | 381/314 |
| 8,144,909 | B2 * | 3/2012 | Hillbratt et al. | 381/326 |
| 2003/0133578 | A1 * | 7/2003 | Durant | 381/60 |
| 2004/0181266 | A1 * | 9/2004 | Wakefield et al. | 607/57 |
| 2005/0096561 | A1 * | 5/2005 | Conn et al. | 600/559 |
| 2005/0107845 | A1 * | 5/2005 | Wakefield et al. | 607/57 |
| 2005/0137650 | A1 * | 6/2005 | Litvak et al. | 607/57 |
| 2007/0055321 | A1 * | 3/2007 | Gordon et al. | 607/55 |
| 2009/0154743 | A1 * | 6/2009 | Lundh et al. | 381/312 |
| 2009/0240307 | A1 * | 9/2009 | Seligman | 607/57 |
| 2009/0247812 | A1 * | 10/2009 | Parker et al. | 600/25 |
| 2009/0292338 | A1 * | 11/2009 | Gordon et al. | 607/57 |
| 2009/0310804 | A1 * | 12/2009 | Parker et al. | 381/314 |
| 2010/0020992 | A1 * | 1/2010 | Flynn | 381/314 |
| 2010/0041940 | A1 * | 2/2010 | Hillbratt et al. | 600/25 |
| 2010/0152813 | A1 * | 6/2010 | Lineaweaver et al. | 607/57 |
| 2010/0280307 | A1 * | 11/2010 | Lineaweaver et al. | 600/25 |

OTHER PUBLICATIONS

International Application No. PCT/US2004/07400, Written Opinion mailed on Aug. 27, 2004, 3 Pages.

International Application No. PCT/US2004/07400, International Search Report mailed on Aug. 27, 2004, 1 Page.

International Application No. PCT/US2004/07400, International Preliminary Report on Patentability dated Mar. 9, 2005, 3 Pages.

Forrest, S., "Genetic Algorithms: Principles of Natural Selection Applied to Computation", Aug. 13, 1993, Science, pp. 872-878, vol. 261, No. 5123.

Official Communication pursuant to Article 94(3) EPC for European Application No. 11722565.6 mailed Aug. 28, 2013 (7 pages).

* cited by examiner

HEARING PROSTHESIS HAVING AN ON-BOARD FITTING SYSTEM

BACKGROUND

1. Field of the Invention

The present invention relates generally to hearing prostheses, and more particularly, to a hearing prosthesis having an on-board fitting system.

2. Related Art

Hearing loss, which may be due to many different causes, is generally of two types: conductive and sensorineural. Sensorineural hearing loss is due to the absence or destruction of the hair cells in the cochlea that transduce sound signals into nerve impulses. Conductive hearing loss occurs when the normal mechanical pathways that provide sound to hair cells in the cochlea are impeded, for example, by damage to the ossicular chain or ear canal. However, individuals suffering from conductive hearing loss may retain some form of residual hearing because the hair cells in the cochlea may remain undamaged.

A variety of hearing prostheses provide therapeutic benefits to individuals suffering from conductive and sensorineural hearing loss. For example, electrically-stimulating hearing prostheses such as auditory brain implants (also referred to as ABIs or auditory brain stimulators) and cochlear implants (also commonly referred to as cochlear prostheses, cochlear devices, cochlear implant devices), provide a person having sensorineural hearing loss with the ability to perceive sound. Such electrically stimulating hearing prostheses bypass the hair cells of the cochlea and deliver an electrical stimulation signal directly to the cochlea, the auditory nerve or the brain.

Another type of hearing prosthesis, referred to as an acoustic hearing aid or simply hearing aid, provides a person having conductive hearing loss with the ability to perceive sound. Acoustic hearing aids deliver amplified acoustic sounds to the ear canal of a recipient. The amplified sounds are relayed to the cochlea via the ossicular chain, resulting in motion of the cochlea fluid that is perceived by the undamaged hair cells.

Another type of hearing prostheses, often generally referred to as mechanical stimulators, mechanically stimulate a recipient. Some mechanical stimulators, such as middle ear implants or direct acoustic stimulators, directly stimulate the middle ear or the oval or round windows of the cochlea. Other prostheses referred to as bone conduction devices indirectly deliver mechanical stimulation to the cochlea by vibrating the recipient's skull.

The effectiveness of a hearing prosthesis depends not only on the prosthesis itself, but also on the success with which the prosthesis is configured for the individual recipient. Configuring hearing prosthesis for a recipient, also referred to as "fitting," "programming" or "mapping," (collectively and generally referred to as "fitting" herein) has traditionally been considered to be a relatively complex process. Typically, a clinician, audiologist or other medical practitioner (generally and collectively referred to as "audiologist" herein) uses interactive software and computer hardware to create individualized programs, commands, data, settings, parameters, instructions, and/or other information (generally and collectively referred to as "fitting data" herein) that are used by the prosthesis to generate the electrical, mechanical and/or acoustic stimulation signals.

SUMMARY

In one embodiment of the present invention, a hearing prosthesis is provided. The hearing prosthesis comprises an external component having a physically integrated input interface comprising: operational control interface having one or more interface elements; a fitting control interface having one or more interface elements, wherein at least one of the fitting control interface elements comprises an operational control interface element; a sound processor configured to process received sounds based on predefined fitting data; and an on-board fitting system configured to set the fitting data in response to control inputs received via the fitting control interface.

In another embodiment of the present invention, a method for fitting a hearing prosthesis to a recipient, the prosthesis comprising a sound processor and an external component having an integrated user interface and an on-board fitting system. The method comprises: receiving a control input via the user interface to initiate the on-board fitting system; receiving replies to output indications provided by the on-board fitting system via the user interface to set fitting data; and receiving a control input via the user interface to deactivate the on-board fitting system.

In a still other embodiment of the present invention, a hearing prosthesis configured to operate in a sound processing mode and a fitting mode is provided. The hearing prosthesis comprises: an external component having an integrated user interface configured to receive user selections of real-time operational parameters of the hearing prosthesis when the hearing prosthesis is in the sound processing mode, and wherein the user interface is configured to receive selections of fitting data when the hearing prosthesis is in the fitting mode; a sound processor configured to process received sounds based on predefined fitting data; and an on-board fitting system configured to set the fitting data in response to control inputs received via the integrated user interface.

BRIEF DESCRIPTION OF THE DRAWINGS

Embodiments of the present invention are described below with reference to the attached drawings, in which.

DETAILED DESCRIPTION

Figure 1:
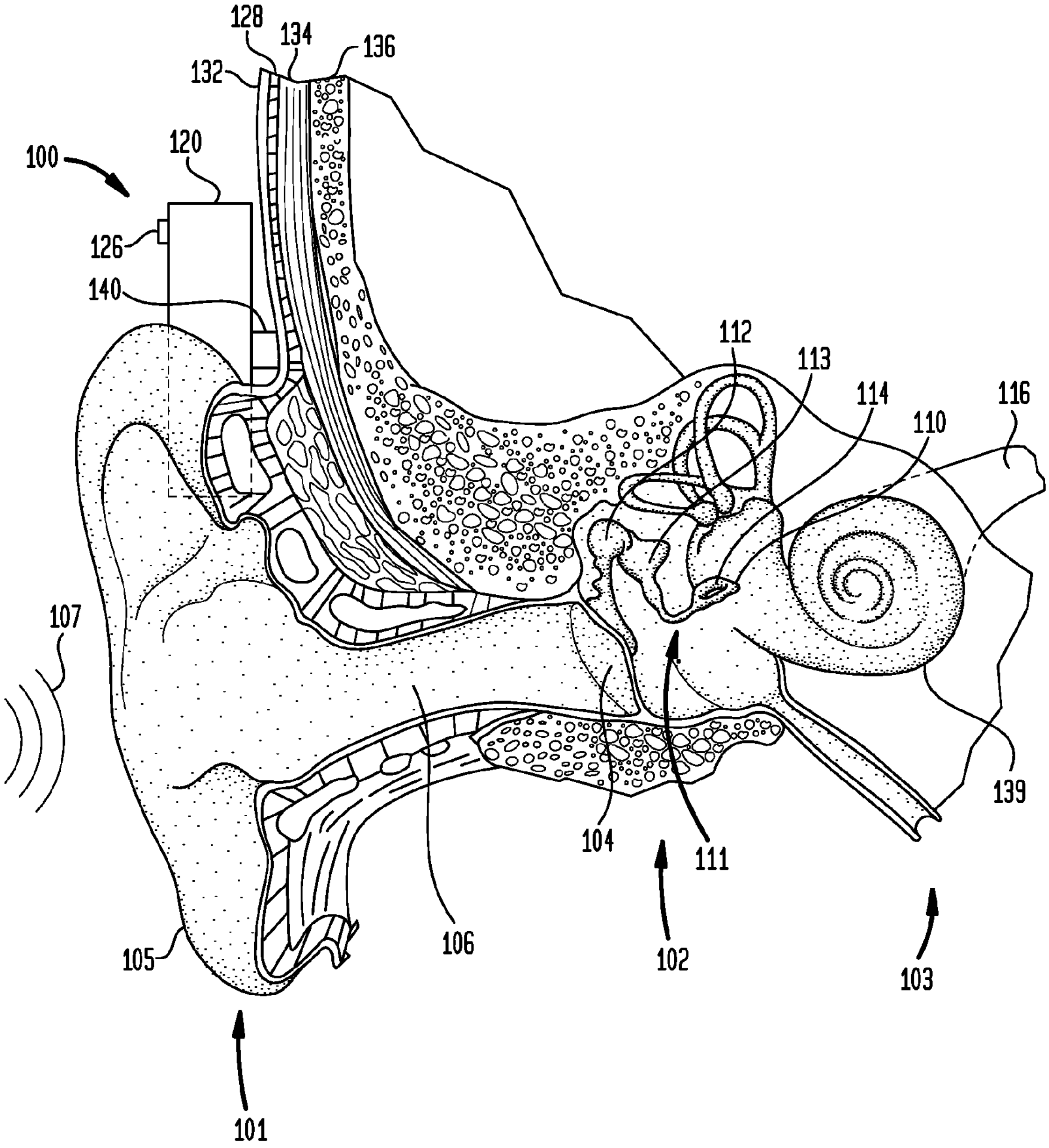
FIG. 1 is a perspective view of an exemplary bone conduction device coupled to a fixation system implanted in a recipient.

Aspects of the present invention are generally directed to a hearing prosthesis having an on-board fitting system controllable via a user interface integrated in an external component of the prosthesis. Implementation of embodiments of the present invention allows fitting of the prosthesis to a recipient via the on-board system without the use of external fitting equipment.

Because the need for external equipment is eliminated, the cost and/or complexity of fitting hearing prostheses implementing embodiments of the present invention is typically less than fitting a conventional hearing prosthesis. In addition, embodiments of the present invention allow fitting to be performed in circumstances in which computerized software and/or clinical support is unavailable. Additional benefits of embodiments of the present invention may vary depending on the particular implementation. For example, some embodiments provide an intuitive and/or simplified fitting procedure conducive to performance by a non-audiologist. In other circumstances, embodiments of the present invention provide a secondary fitting procedure that may support or supplement external fitting equipment.

Hearing prostheses in accordance with embodiments of the present invention have several operational states or modes. In one operational state or mode, referred to herein as the fitting mode, the hearing prosthesis is fit to an individual recipient by adjusting or generating fitting data. That is, during the fitting mode, data that is used to process sound, generate stimulation signals, etc., are determined and stored in the prosthesis.

In another operational state or mode, referred to herein as the sound processing mode, the hearing prosthesis delivers stimulation in response to a detected sound. When in the sound processing mode, the prosthesis processes sound and generates stimulation signals in accordance with stored fitting data. While in the sound processing mode, hearing prostheses commonly provide a recipient with the ability to adjust, select or otherwise control real-time operational parameters, such as volume, while the prosthesis is in the sound processing mode. An operational control user interface is provided for such real-time adjustment of operational parameters. Oftentimes, the operational control interface is at least in part physically integrated into the external component of the hearing prosthesis.

As previously noted, a hearing prosthesis in accordance with embodiments of the present invention also includes a fitting control user interface. In certain embodiments of the present invention, the fitting control interface is separate from the operational control interface; that is, the two interfaces do not share the same interface elements. In other embodiments, one or more of the same interface elements are utilized in both the fitting control interface and the operational control interface. In specific embodiments, all interface elements of the operational control interface are also shared by the fitting control interface.

As previously noted, a number of different hearing prostheses have been developed to rehabilitate a recipient's hearing. The different prostheses may have different configurations and may comprise combinations of internal (implantable) and external components, or solely external or internal components. Of particular interest are prostheses comprising one or more external components. One such prosthesis having an external component is a bone conduction device that, as noted above, indirectly delivers mechanical stimulation to a recipient's cochlea by vibrating the recipient's skull. For ease of description, embodiments of the present invention are described herein with reference to an exemplary hearing prosthesis, a bone conduction device.

FIG. 1 is a perspective view of an exemplary bone conduction device 100 attached to a recipient. The exemplary recipient of FIG. 1 has an outer ear 101, a middle ear 102 and an inner ear 103. However, it would be appreciated that other recipient's may have missing or deformed middle or outer ears.

In a fully functional human ear, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 139. Such fluid motion, in turn, activates tiny hair cells (not shown) that line the inside of cochlea 139. Activation of the hair cells causes appropriate nerve impulses to be transferred through spiral ganglion cells (not shown) to auditory nerve 116 and ultimately to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient and comprises a housing 120. A sound input element 126 is positioned in or on housing 120 and is configured to receive sound signals. Sound input element 126 may comprise, for example, a microphone, telecoil, etc. It should be appreciated that bone conduction device 100 may comprise more than one sound input device.

As described below, bone conduction device 100 comprises a sound processor, a transducer that outputs vibration, and/or one or more other components which facilitate operation of the device. Bone conduction device 100 operates by converting sound signals 107 received by microphone 126 into electrical signals. These electrical signals are converted by the sound processor into control signals for use by the transducer. The transducer vibrates in response to such control signals, which in turn causes vibration of the recipient's skull.

Bone conduction device 100 further includes a coupling 140 configured to attach the device to the recipient. Coupling 140 is attached to an anchor system (not shown) implanted in the recipient. An exemplary anchor system (also referred to as a fixation system) may include a percutaneous abutment fixed to the recipient's skull bone 136. The abutment extends from bone 136 through muscle 134, fat 128 and skin 132 so that coupling 140 may be attached thereto.

Figure 2A:
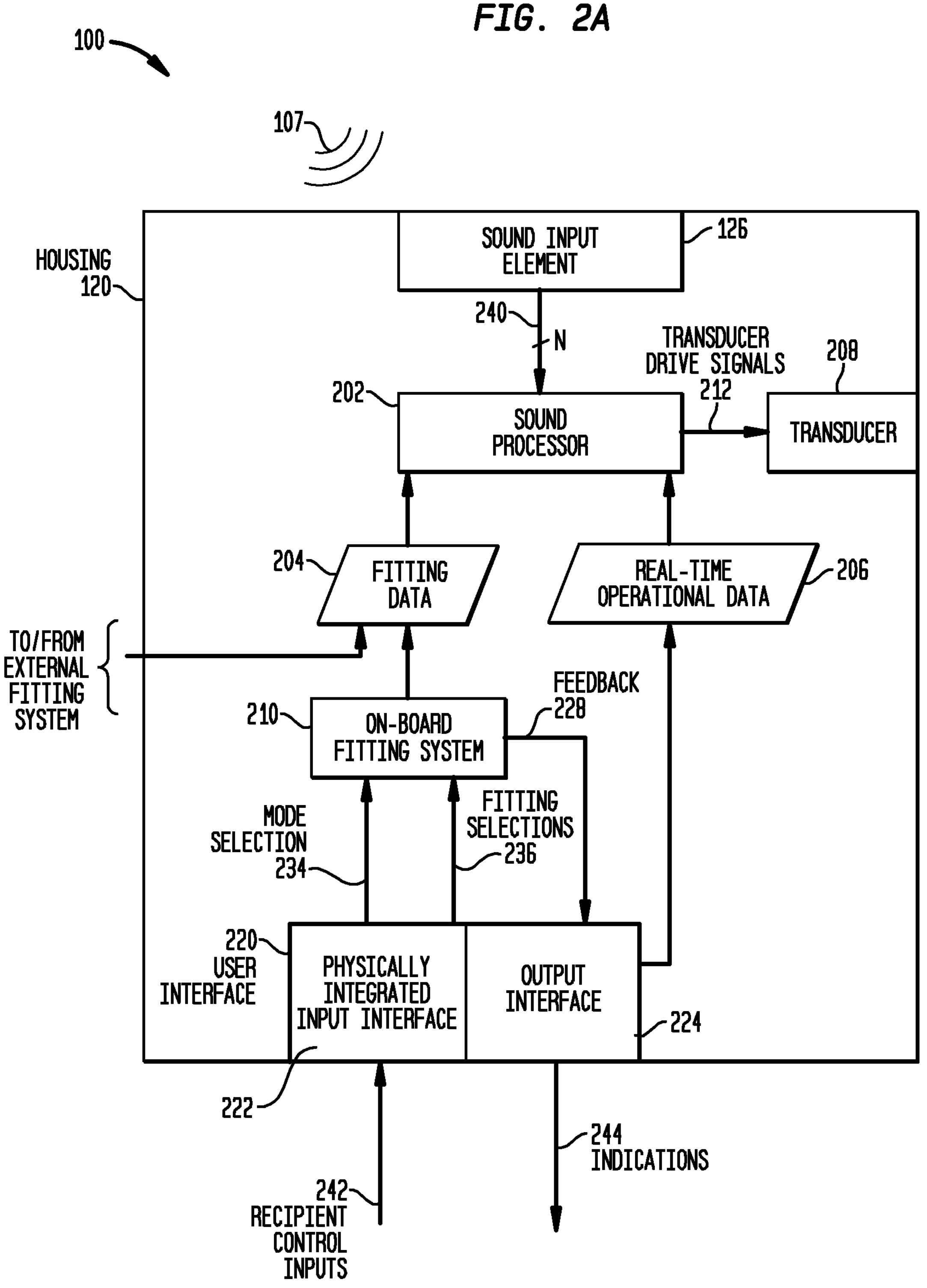
FIG. 2A is a functional block diagram of a bone conduction device in accordance with embodiments of the present invention.

FIG. 2A is a functional block diagram of embodiments of bone conduction device 100 of FIG. 1. As noted, device 100 may operate in a sound processing mode and a fitting mode. In the sound processing mode, sound input element 126 receives a sound signal 107 and converts it into one or more electrical signals 240 indicative of the received sound signal. Signals 240 are processed by a sound processor 202, and converted to transducer drive signals 212. Drive signals 212 cause actuation of transducer 208 that results in vibration of the recipient's skull.

In certain embodiments sound processor 202 controls the overall function of bone conduction device 100. For example, sound processor 202 may control the device volume or gain, selectively enhance and limit the amplitude of certain sound frequencies, etc. In alternate embodiments, sound processor 202 has a more limited functionality, and other control elements are utilized with sound processor 202. For example, a separate volume control unit may be provided which receives output from the sound processor 202, and, in-turn, outputs transducer drive signal 212.

In a fitting mode of bone conduction device 100, fitting data 204 is stored within bone conduction device 100. Fitting data 204 may include, for example, a selection of the side of the head on which bone conduction device 100 will be worn (sometimes referred to herein as side selection parameter), gain parameters, a section to turn on or off certain device functionality (sometimes referred to herein as functionality parameters) or other parameters used by sound processor 202 to convert signals 240 to transducer drive signals 212. Fitting date for selecting the side of the head is described in greater detail below. In certain circumstances, fitting data 204 may be received from an external fitting system (not shown), such as a personal computer, clinic based fitting system, etc. However, in other circumstances, fitting data 204 may be generated by an on-board fitting system 210 in response to inputs received from a user interface 220.

As shown, user interface 220 comprises a physically integrated input interface 222, and an output interface 224. Physically integrated input interface 222 is integrated as a component of bone conduction device 100, and is not a separate external component. As detailed below, in certain embodiments, interface elements of physically integrated input interface 222 are integrated in housing 120, while the supporting circuitry and/or software of the physically integrated input interface 222 are located within the housing 120. As used herein, integrated in device 100 refers to components or elements that are in or on housing 120.

In an exemplary fitting procedure of FIG. 2A, physically integrated input interface 222 functions as a fitting control interface and receives recipient control inputs 242 from the recipient. To begin the fitting procedure, the recipient enters an input 242 that initiates on-board fitting system 210, represented by mode selection signal 234. Additionally, during the fitting procedure, the recipient enters one or more other inputs 242 that cause on-board fitting system 210 to generate or adjust fitting data 204, shown as fitting selections 236. The types of inputs entered by the recipient, and the resulting adjustments, are described further below.

The function of on-board fitting system 210 is to generate fitting data 204 from the inputs received via physically integrated input interface 222. In certain embodiments, on-board fitting system 210 may utilize a lookup table or the like to compare the signals from the user interface 220 to identify the appropriate fitting data parameters that should be set in the bone conduction device.

As noted above, in accordance with embodiments of the present invention, user interface 220 may comprise a fitting control interface, as well as an operational control interface. That is, user interface 220 is configured to control adjustment of fitting data 204, and adjustment of real-time operational data 206. Operational data 206 may include, for example, the volume of the device. Such operational data 206 may be adjusted during a sound processing mode through entry of certain recipient control inputs 242.

As shown in FIG. 2A, user interface 220 further comprises an output interface 224 that provides indications 244 to a recipient. In certain embodiments, indications 244 may be generated by the user interface 220 as a result of feedback 228 from on-board fitting system 210. As will be described in greater detail below, indications 244 may include indications relating to the generation of fitting data 204 and/or the adjustment of real-time operational data 206.

Figure 2B:
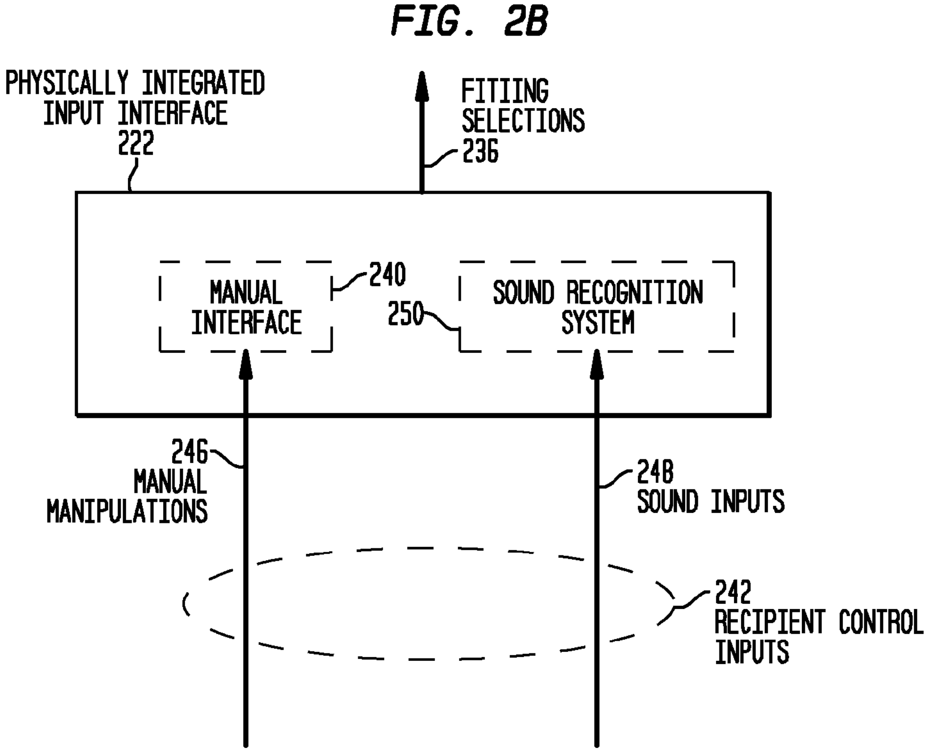
FIG. 2B is a functional block diagram of embodiments of the physically integrated input interface illustrated in FIG. 2A.

FIG. 2B is a functional block diagram of embodiments of physically integrated input interface 222 of FIG. 2A configured to receive recipient control inputs 242. In certain embodiments of the present invention, recipient control inputs 242 are manual manipulations 246 of interface elements of a manual interface integrated into housing 120 (FIG. 2A) of bone conduction device 100. In certain embodiments, elements of manual interface 240 may comprise buttons positioned on housing 120. In other embodiments, elements of manual interface 240 may comprise a scroll wheel, slide pad, roller ball, dial, touch screen (ie. capactive or resistive sensine elements), switch or other type of manually adjustable device. In still other embodiments, elements of manual interface 240 may comprise heat sensing "buttons" or optical sensing "buttons." In such embodiments, manual interface 240 may not include moving parts, but instead sense heat, electrical voltage or a reduction in ambient light resulting from, for example, a recipient touching those buttons.

In embodiments of the present invention, the same interface elements (buttons, controls, etc) may used to adjust fitting data 204 and real-time operational data 206. That is, in certain embodiments one or all of the interface elements used as the fitting control interface may also be used as the operational control interface. Additionally, it would be appreciated that the number of inputs that may be entered by the recipient is not limited to the number of buttons or controls provided. Specifically, a recipient may enter different inputs by manipulating different combinations of interface elements In other embodiments, recipient control inputs 242 may comprise sounds input 248 received by a fitting control interface in the form of a sound recognition system 250. In an exemplary embodiment, sound recognition system 250 may include a sound input element that receives audible signals or commands from a recipient. System 250 interprets the signals, and outputs fitting selections signal 236 based thereon. In an exemplary embodiment, the sound input element may be the sound input element 126 of the bone conduction device 100, and sound recognition system 250 may be responsive to the recipient's voice, a specific verbal code, specific audible tones or sequences of tones, etc. In an exemplary embodiment, physically integrated input interface 222 includes one or both of the manual interface 240 and the sound recognition system 250.

Figure 2C:
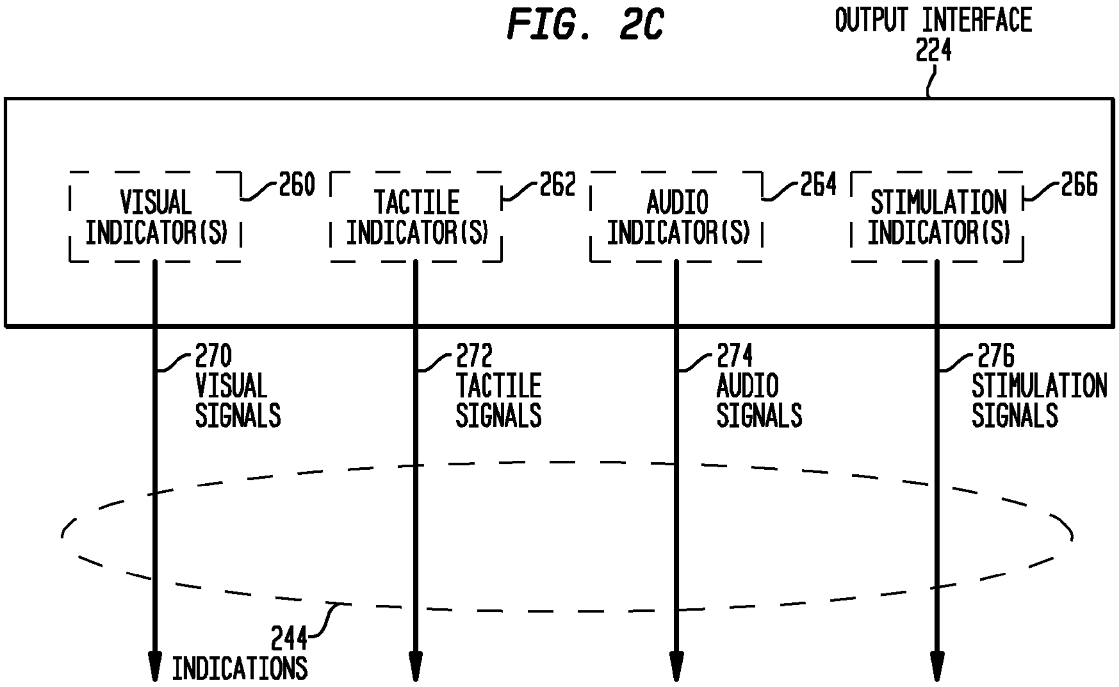
FIG. 2C is a functional block diagram of embodiments of the output interface illustrated in FIG. 2A.

FIG. 2C presents a functional diagram of embodiments of output interface 224 of FIG. 2A configured to output indicators 244. In certain embodiments of the present invention, indicators 244 may comprise visual signals 270 output by visual indicator(s) 260. Visual indicator(s) 260 may comprise, for example, light emitting diodes (LEDs), an LCD screen, incandescent bulbs, a color coded wheel (e.g., a portion of the wheel may be viewed through a port), or other device that will output a visual signal. In other embodiments, indications 244 may comprise tactile signals 272 output by tactile indicator(s) 262. Tactile indicator(s) 262 may comprise, for example, vibrations generated by transducer 208 which vibrate housing 120, and which are felt by the recipient.

As is further illustrated in FIG. 2C, indications 244 output by output interface 224 may be in the form of audio signals 274 from audio indictor(s) 264. Audio indicator(s) 264 may comprise, for example, a speaker that outputs words, phrases, tones, beeps, etc. In other embodiments, indications 244 may be stimulation signals 276 output by stimulation indicator(s) 266. Stimulation signals 276 may comprise, for example, vibrations generated by transducer 208 for delivery to the skull. In other specific embodiments of electrically stimulating hearing prosthesis or mechanical stimulators, stimulation signals 276 comprise electrical stimulation signals or mechanical stimulation signals, respectively.

Figure 3:
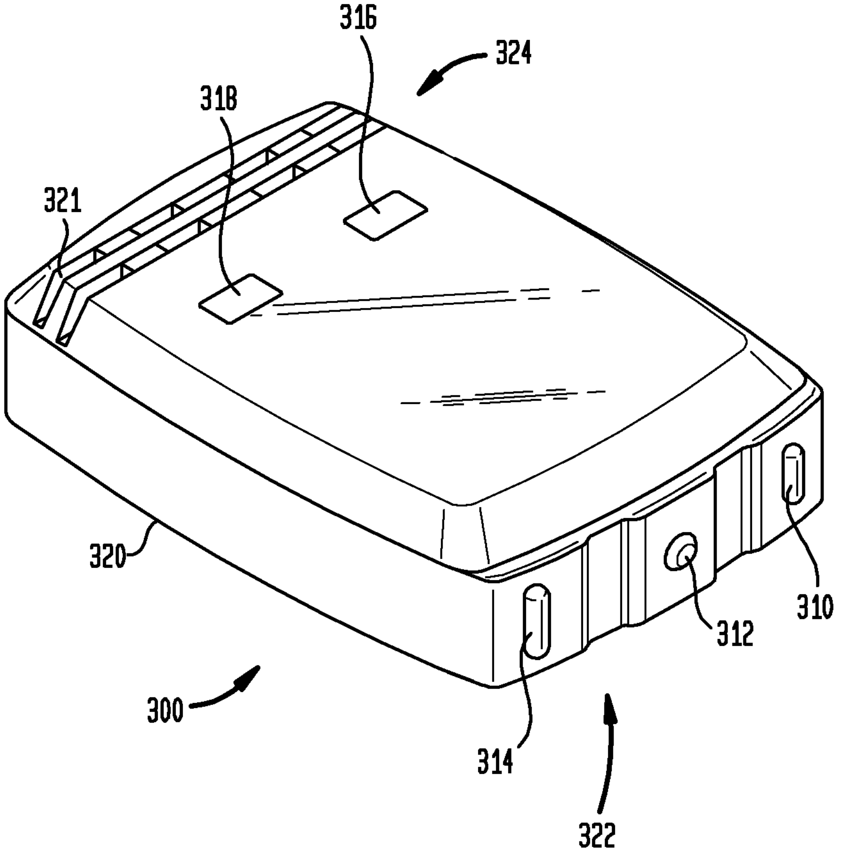
FIG. 3 is a perspective view of a bone conduction device in accordance with embodiments of the present invention.

FIG. 3 is a perspective view of embodiments of bone conduction device 100 described above, referred to as bone conduction device 300. Similar to the above embodiments, bone conduction device 300 includes a user interface physically integrated into housing 320. Specifically, the user interface comprises physically integrated input interface 322 and output interface 324. Physically integrated input interface 322 (hereinafter "input interface" 322) include three buttons 310, 312 and 314. When in the sound processing mode noted above, button 310 and 314 are volume control buttons 310 and 314, while button 312 is a program button 312. The recipient presses button 314 to increase the volume of the sound perceived by a recipient (hereinafter "volume"), while button 310 is used by a recipient to decrease the volume. However, it would be appreciated that in other embodiments the functionality of buttons 314 and 310 may be reversed. As described below, programming button 312 is used in conjunction with buttons 314 and 310 during the fitting mode.

As illustrated in FIG. 3, output interface 324 includes visual indicators 316 and 318 which comprise two separate LEDs 318 and 316. Output interface 324 may also comprise audio output device 321, which, in an exemplary embodiment, is a speaker.

Figure 4A:
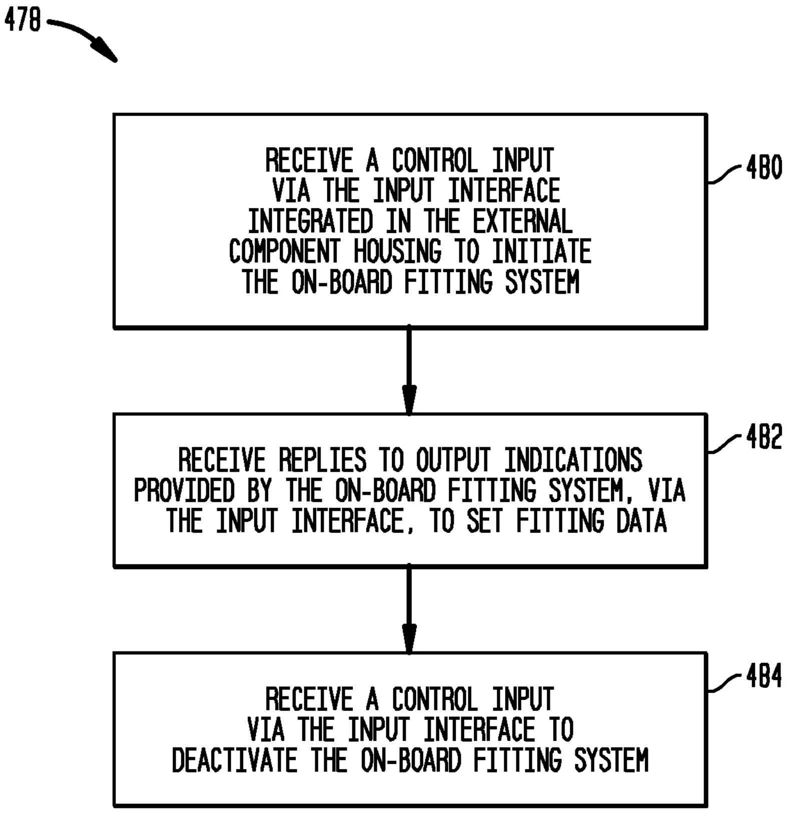
FIG. 4A is a high level flowchart illustrating operations performed during an exemplary fitting process in accordance with embodiments of the present invention.
Figure 4B:
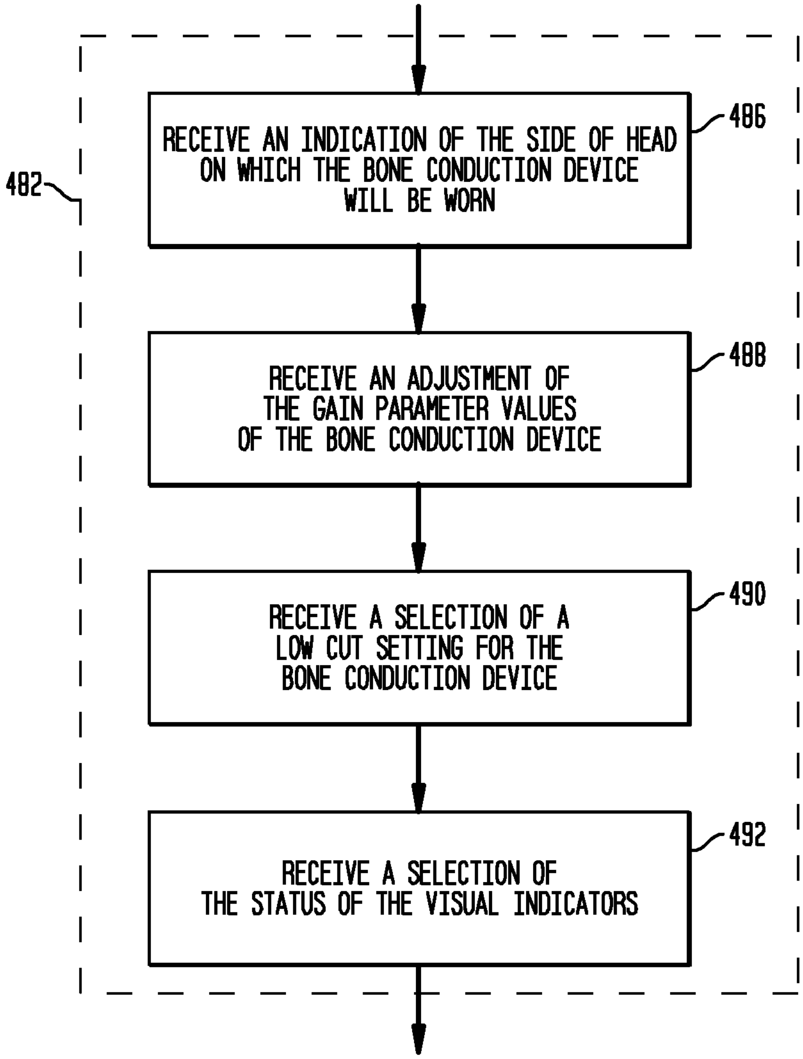
FIG. 4B is a detailed flowchart illustrating the operations performed to enter fitting data, in accordance with embodiments of the present invention.

As previously noted, fitting of a bone conduction device for a recipient may be performed using an on-board fitting system and a user interface integrated into the device. FIG. 4A is a high level flowchart illustrating operations performed during an exemplary fitting process 478 to fit device 300 (FIG. 3) to a recipient. FIG. 4B is a detailed flowchart illustrating one specific embodiment of process 478. For ease of description, the steps of FIGS. 4A and 4B will be described with reference to FIGS. 5A-5L that provide top and/or side views of bone conduction device 300.

Figure 5A:
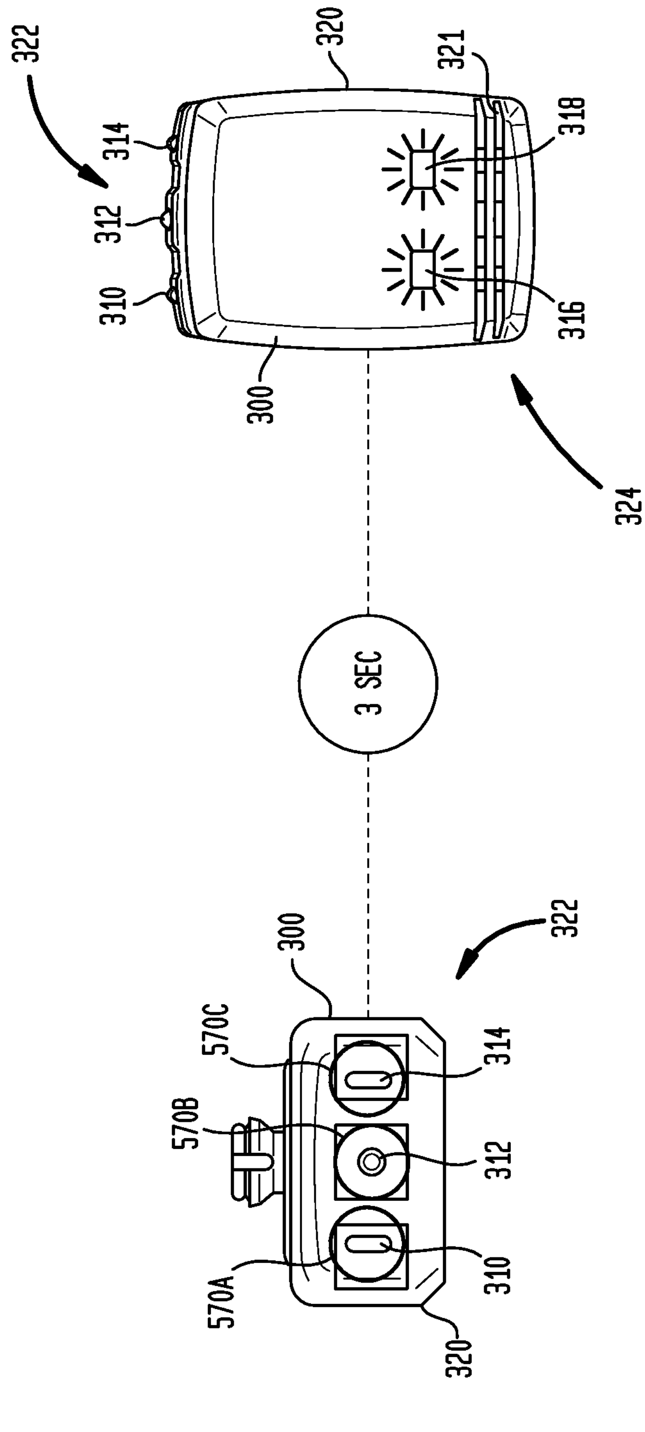
FIG. 5A is a top and side view of a bone conduction device, in accordance with embodiments of the present invention.

As shown, on-board fitting process begins at step 480 where a control input initiating the on-board fitting system is received via the integrated user interface. Specifically, as shown in FIG. 5A, in step 480 the recipient initiates on-board fitting process by simultaneously pressing and holding buttons 310, 312 and 314. The pressing of buttons 310, 312 and 314 is schematically represented in FIG. 5A by circles 570A, 570B and 570C surrounding each button in the top view of device 300. In certain embodiments, fitting process 478 is initiated by pressing buttons 310, 312 and 314 for approximately three seconds.

When the recipient presses buttons 310, 312 and 314, visual indicators 316 and 318 display a series of flashes verifying the initiation. In one embodiment, the series of flashes comprise a single long flash from each indicator 316, 318, followed a series of short flashes alternating between the indicators. These flashes are schematically shown by the lines extending from indicators 316 and 318 in the side view of FIG. 5A.

After the on-board fitting process is initiated, at step 482, the recipient sets one or more fitting data parameters for device 300 by variously pressing buttons 310, 312 and 314 in a predetermined manner. More specifically, as described further below with reference to FIG. 4B, the system receives recipient replies to a series of output indications provided by on-board fitting system via visual indicators 316 and 318. After the fitting data parameters are selected, the device receives an indication to deactivate the on-board fitting system at block 484.

In certain embodiments, on-board fitting system 210 may be deactivated in substantially the same manner as it is initiated at step 480. Specifically, as shown in the top view of device 300 in FIG. 5J, the recipient presses and holds buttons 310, 312 and 314 for three seconds. This causes visual indicators 316 and 318 to stop flashing, thereby providing an indication that the on-board fitting system was deactivated.

As noted above, the recipient sets one or more fitting data parameters during step 482. FIG. 4B illustrates one exemplary set of processes that may be implemented during step 482 of FIG. 4A.

The exemplary processes of FIG. 4B start at step 486, where the devices receives an indication of which side of the head bone conduction device 300 is to be worn. That is, at step 486 the recipient sets a fitting parameter corresponding to the side of the head on which the recipient will wear device 300.

Figure 5B:
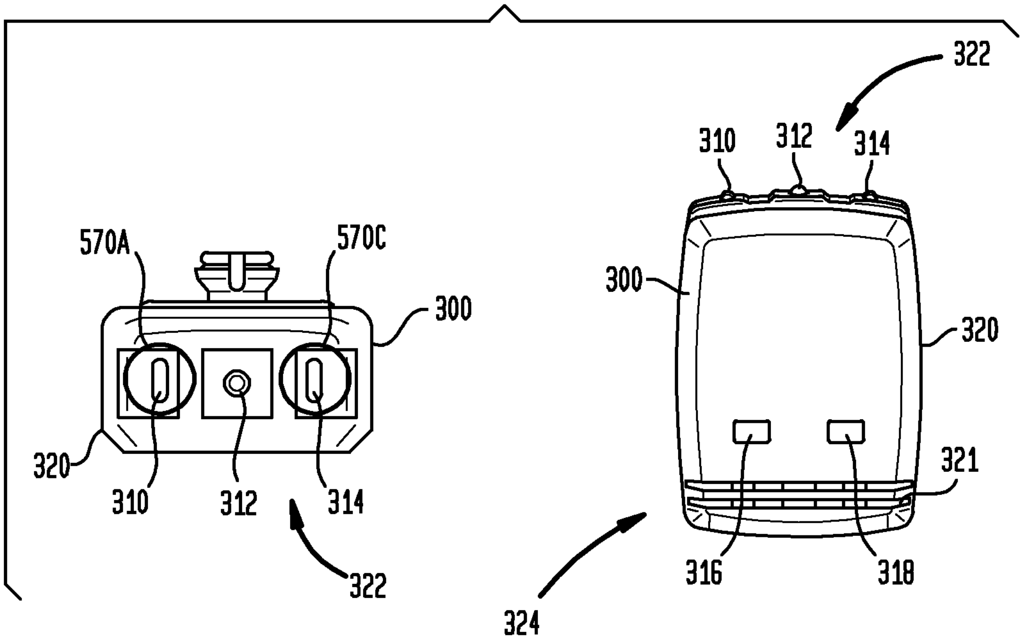
FIG. 5B is a top and side view of a bone conduction device, in accordance with embodiments of the present invention.

In step 486, the recipient selects the desired side of the head by pressing one of the buttons 314 or 310. In the arrangement of FIG. 5B, the recipient selects the left side of the head by pressing button 314, causing visual indicator 316 to illuminate. In contrast, the recipient may select the right side of the head by pressing button 310. This causes visual indicator 318 to illuminate.

The side fitting data parameter is used by bone conduction device 300 to, among other things, to set the directionality of the device. For example, bone conduction device 300 may include one microphone that, when the device is worn by the recipient, faces forward and a microphone that faces backward. In one embodiment, the sound processor only processes sound from the microphone that faces forward (as that is the most likely direction from which someone will talk to the recipient). Accordingly, by setting the side fitting data parameter, one of the two microphones will be disabled, depending on which side of the recipient the bone conduction device is to be used. In an alternate embodiment, the sound processor may process sound received by both microphones. In such embodiments, the sound process may apply weighting factors to the sound received by each of the microphones, depending upon the side fitting parameter selected by the recipient.

The selection of the side of head in accordance with embodiments of the present invention may be implemented in a variety of manners. In one exemplary embodiment, the selection is through actuation of a switch disposed on the bone conduction device.

Figure 5C:
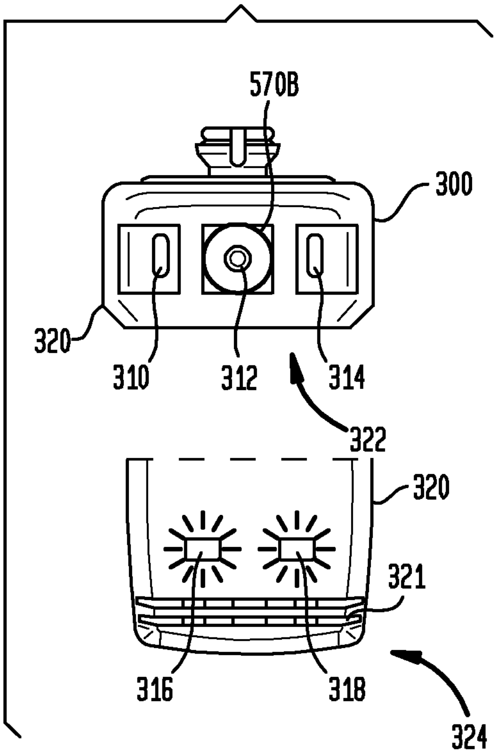
FIG. 5C is a top and side view of a bone conduction device, in accordance with embodiments of the present invention.

As shown in FIG. 5C, after the desired side parameter is selected, the user stores the parameter by pressing program button 312. This causes both visual indicators 316 and 318 to each output two flashes followed by a series of short, alternating flashes, thereby allow the recipient to confirm the parameter was stored.

Following confirmation that the selected side fitting data parameter has been stored, the process advances to step 488 where the device receives an adjustment of a gain curve fitting data parameter of device 300. In other words, the recipient may adjust gain curves that will be utilized by the device to convert sound signals into skull vibrations. In certain embodiments, a default value for a gain curve fitting data parameter is provided, and the recipient may increase the gain 5 dB above the default value, or alternatively, decrease the gain 5 dB below the default value.

Figure 6:
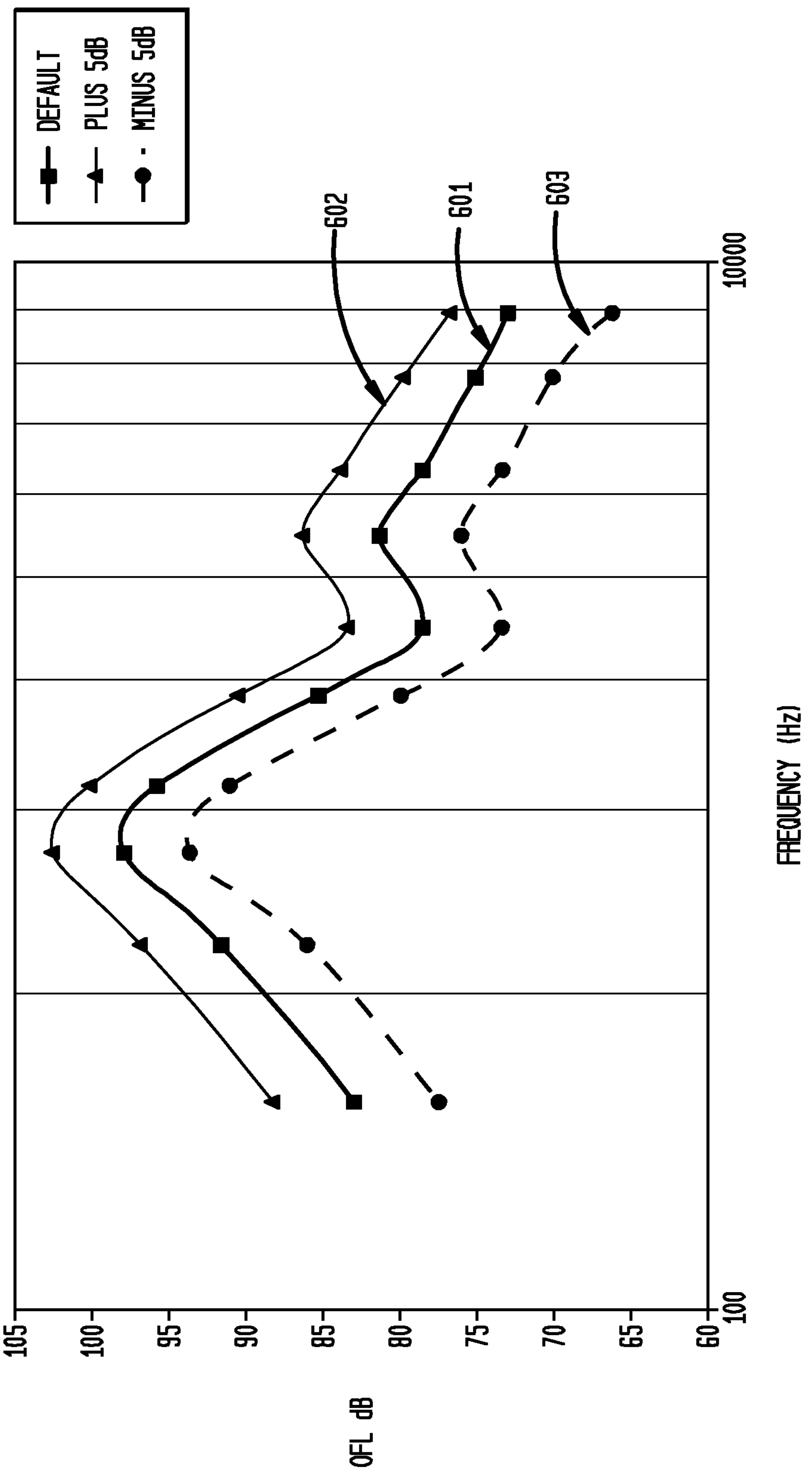
FIG. 6 is a graph of exemplary gain curves that may be implemented in embodiments of the present invention.

FIG. 6 is a graph illustrating a default gain curve 601 extending across a range of sound frequencies generated by the bone conduction device 300 based on a default gain curve fitting data parameter. Adjusting the gain curve fitting data parameter at step 488 to increase the gain of the gain curve increases the gain by 5 dB across the depicted frequencies, thereby resulting in curve 602. Adjusting the gain curve fitting data parameter at step 488 to decrease the gain decreases the gain by 5 dB across the depicted frequencies, thereby resulting in curve 603. It will be appreciated that adjustment of the gain curve by 5 dB is illustrative and that in some embodiments the gain curve may be adjusted upwards and/or downwards in other increments.

Figure 5D:
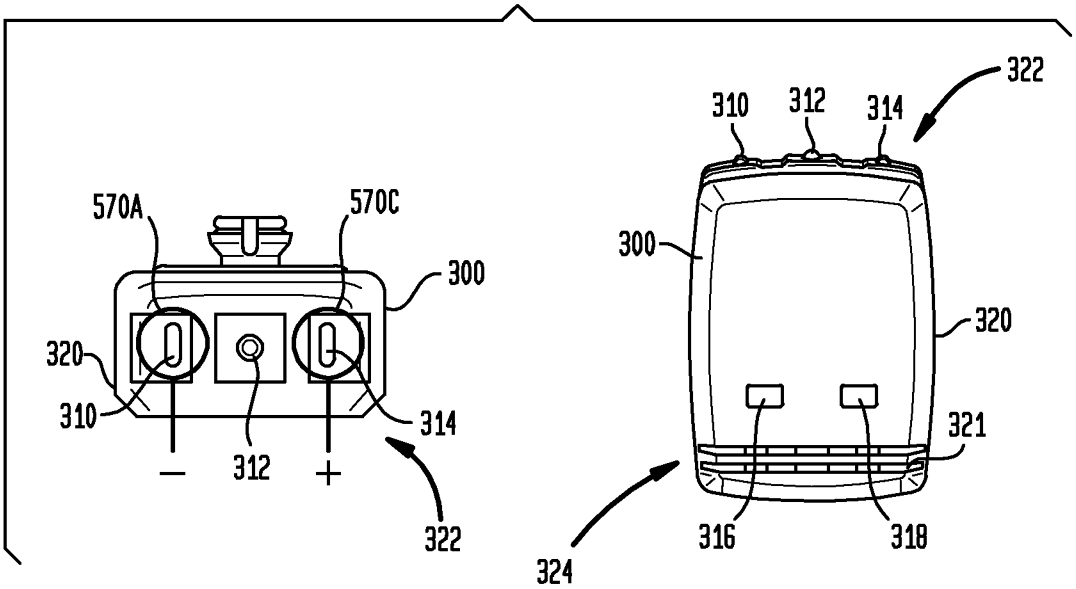
FIG. 5D is a top and side view of a bone conduction device, in accordance with embodiments of the present invention.

As shown in FIG. 5D, the gain curve fitting data parameter may alternatively be adjusted to decrease the gain from the default gain curve 601 by pressing button 310. This will cause visual indicator 316 to illuminate. In contrast, the recipient may adjust the gain curve fitting data parameter to increase the gain from the default gain curve 601 by pressing button 314. This causes visual indicator 318 to illuminate. To return to the default gain curve fitting data parameter setting, the recipient simultaneously presses buttons 314 and 310, thereby causing both indicators 316 and 318 to illuminate.

Figure 5E:
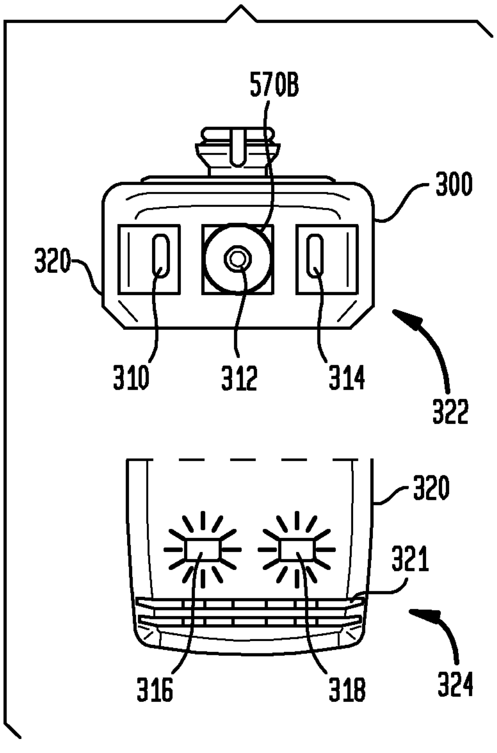
FIG. 5E is a top and side view of a bone conduction device, in accordance with embodiments of the present invention.

As shown in FIG. 5E, the user stores the gain curve fitting data parameter by pressing program control 312. This causes visual indicators 316 and 318 to each output two flashes followed by a series of short, alternating flashes, thereby allowing the recipient to confirm the parameter has been stored.

In one alternative embodiment, a recipient may press buttons 310 and 314 for a period of time to effect the desired change in the gain curve fitting data parameter. For example, the recipient may press button 310 for a period of two seconds to adjust the gain curve fitting data parameter to decrease the gain curve by two increments (e.g., from gain curve 602 to gain curve 603). Alternatively, the recipient may press button 310 two separate times to adjust the gain curve fitting data parameter to decrease the gain curve by the same two increments.

Returning to the embodiments of FIG. 4B, after setting the gain curve fitting data parameter, the gain curve may be further adjusted by optionally receiving a selection of a low cut fitting data parameter at step 490. That is, the recipient may cause the device to operate in a low cut mode, or in default mode. In the low cut mode, the gain of the device is attenuated in the lower frequencies as compared to the default mode.

Figure 7:
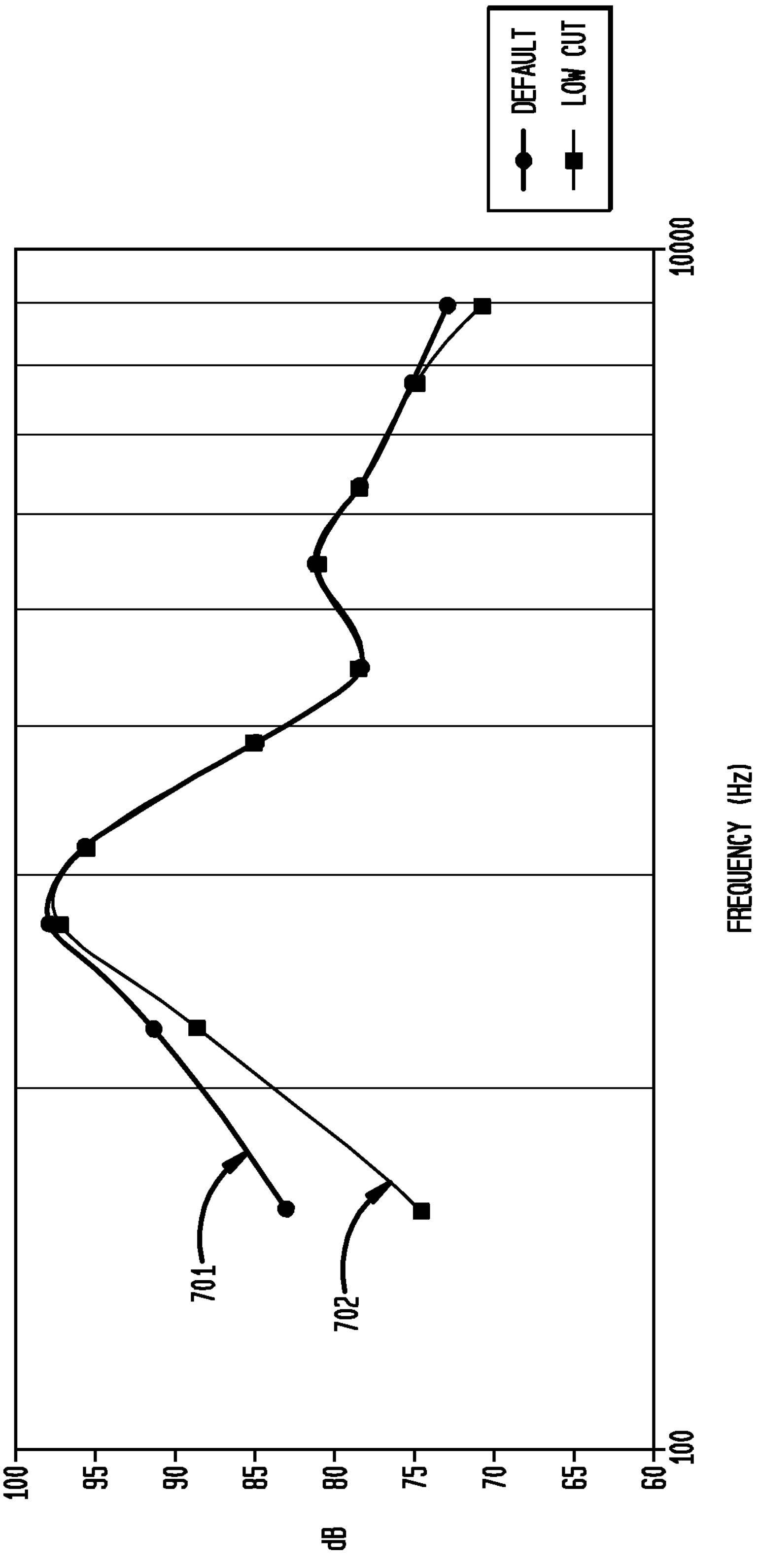
FIG. 7 is a graph of a gain curve of a low cut mode of operation utilized in embodiments of the present invention.

FIG. 7 is a graph illustrating a gain curve 701 over a range of sound frequencies in a default mode of bone conduction device 300, and a gain curve 702 over that same range of frequencies when the bone conduction device is operating in the low cut mode. As may be seen in FIG. 7, when in the low cut mode, the gain of the lower frequencies is reduced by as much as 9 dB as compared to the default settings. However, in low cut mode, the gain in the mid to high range frequencies is substantially the same as in the default mode, with a slight downward deviation at the high frequencies.

Figure 5F:
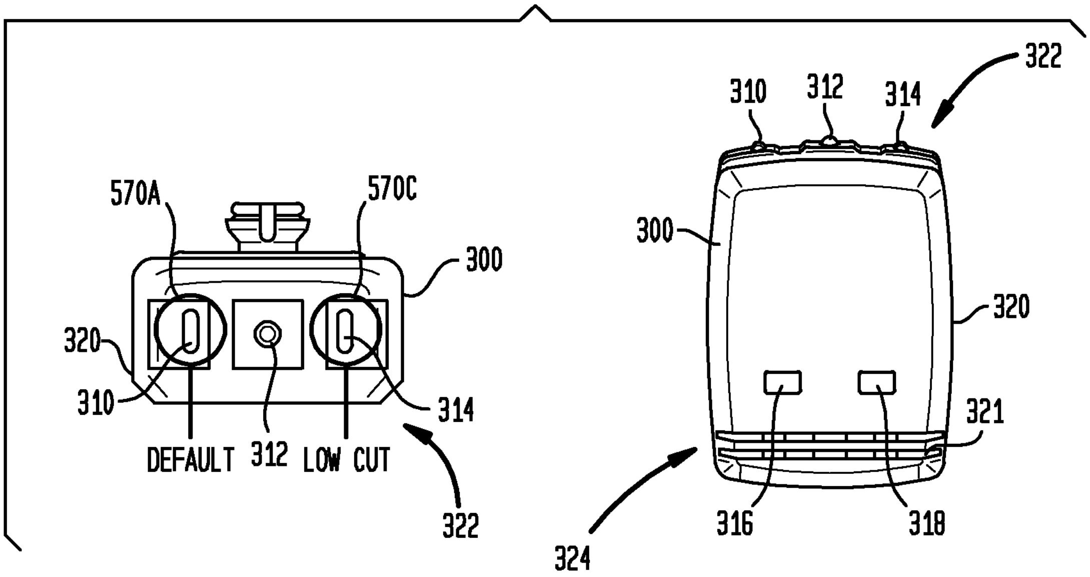
FIG. 5F is a top and side view of a bone conduction device, in accordance with embodiments of the present invention.
Figure 5G:
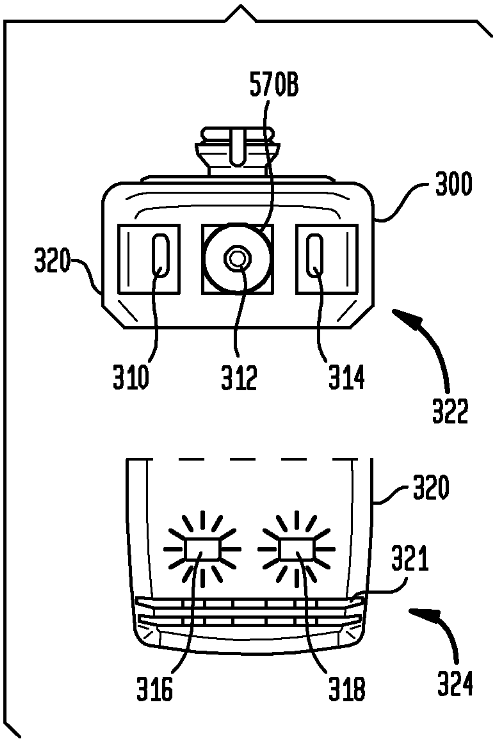
FIG. 5G is a top and side view of a bone conduction device, in accordance with embodiments of the present invention.

As shown in FIG. 5F, the default mode is selected by pressing button 310. This will cause visual indicator 316 to illuminate. In contrast, the recipient may change the low cut fitting data parameters by pressing button 314, to select the low cut mode. This causes visual indicator 318 to illuminate. Furthermore, as shown in FIG. 5G, the recipient stores the selected low cut fitting data parameters by pressing button 312. This causes visual indicators to each output two flashes followed by a series of short, alternating flashes, which allow the recipient to confirm the low cut fitting data parameters have been stored, and that the bone conduction device 300 will operate in the low cut mode or the default mode when in the sound processing operational mode.

Returning to FIG. 4B, at step 492 the device may receive a selection of the status of visual indicators 316 and 318 prior to completion of the fitting process 478. Specifically, the recipient may select an indication fitting data parameter such that output interface 324 will not provide indications to the recipient following completion of fitting process 478. Alternatively, the recipient may select an indication fitting data parameter such that output interface 324 will provide indications after completion of fitting process 478.

Figure 5H:
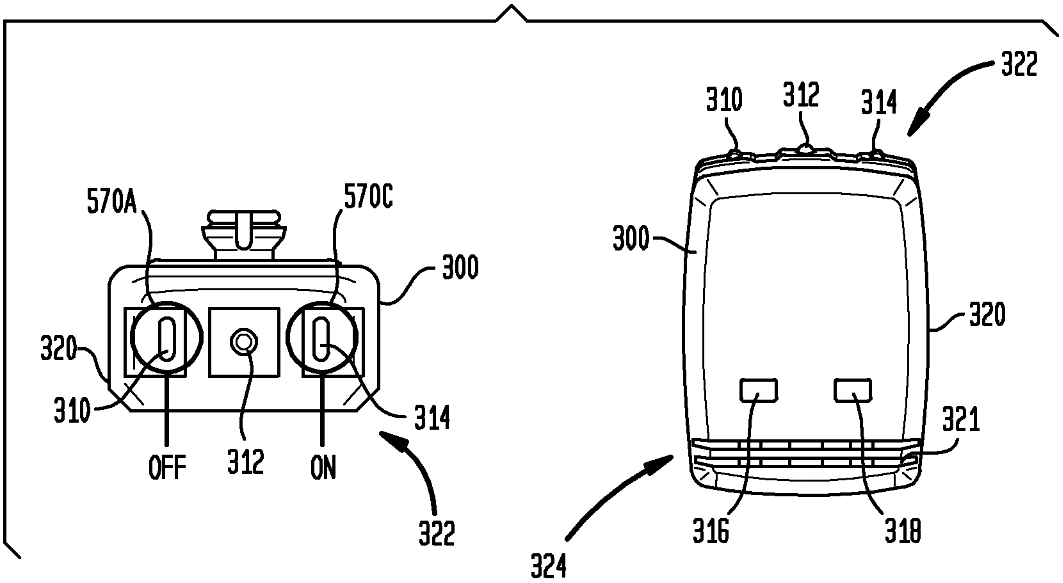
FIG. 5H is a top and side view of a bone conduction device, in accordance with embodiments of the present invention.
Figure 5I:
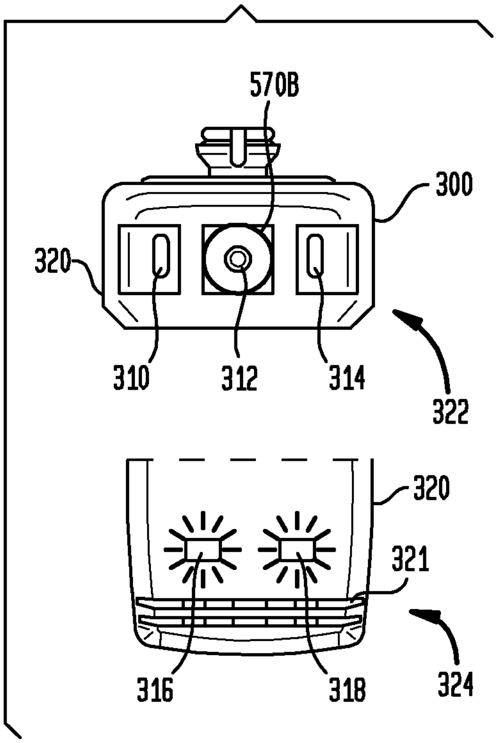
FIG. 5I is a top and side view of a bone conduction device, in accordance with embodiments of the present invention.
Figure 5J:
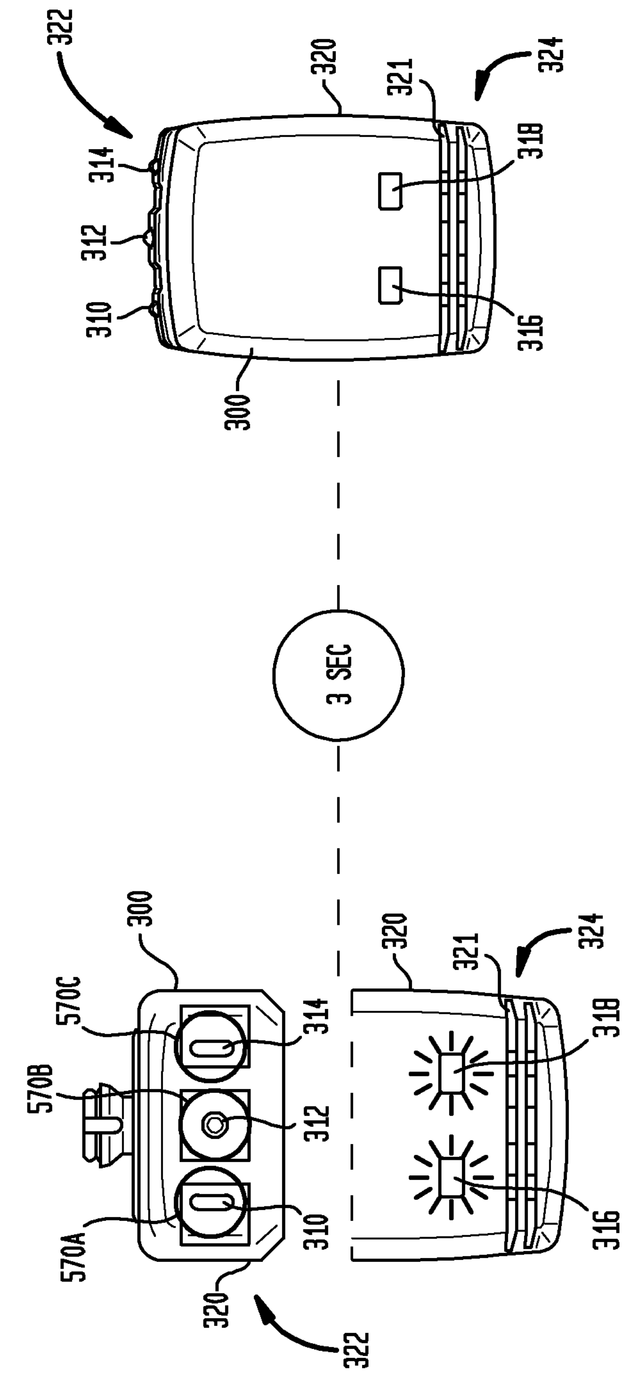
FIG. 5J is a top and side view of a bone conduction device, in accordance with embodiments of the present invention.

As shown in FIG. 5H, the indication fitting data parameter is set to turn off LEDs 316, 318 and/or speaker 321 by pressing button 310. This will cause visual indicator 316 to illuminate. In contrast, the recipient may set the indication fitting data parameter to an on configuration by pressing button 314. This causes visual indicator 318 to illuminate. Furthermore, as shown in FIG. 5I, the user stores the selected indication fitting data parameter by pressing program control 312. This causes visual indicators to each output two flashes followed by a series of short, alternating flashes, thereby allowing the recipient to confirm the mode has been stored. Following storage of this final parameter, the fitting process returns to block 484 of FIG. 4A for deactivation of the on-board fitting system. In alternative embodiments, the recipient has the option to re-perform steps 486-492 to change any of the selected parameters.

As previously noted, the steps of FIG. 4B are merely illustrative. As such, one or more these may be omitted and/or other fitting steps may be included. For example, in certain embodiments the fitting data includes the selection of a functionality parameter. In these embodiments, the on-board fitting system turns on or off certain functionality, such as beamforming, power saving operations, etc., based on a user input.

In certain embodiments of the present invention, following completion of fitting process 478, bone conduction device 300 may be placed into a tamper proof or key lock mode. The key lock mode locks the controls of bone conduction device 300 so that pressing buttons 310, 312 and/or 314 will have no effect. Depending on the embodiment, the key lock mode may or may not be part of the fitting process. That is, in some embodiments, to enter the key lock mode, the on-board fitting system must be activated, while in other embodiments the key lock mode may be initiated at any time.

Figure 5K:
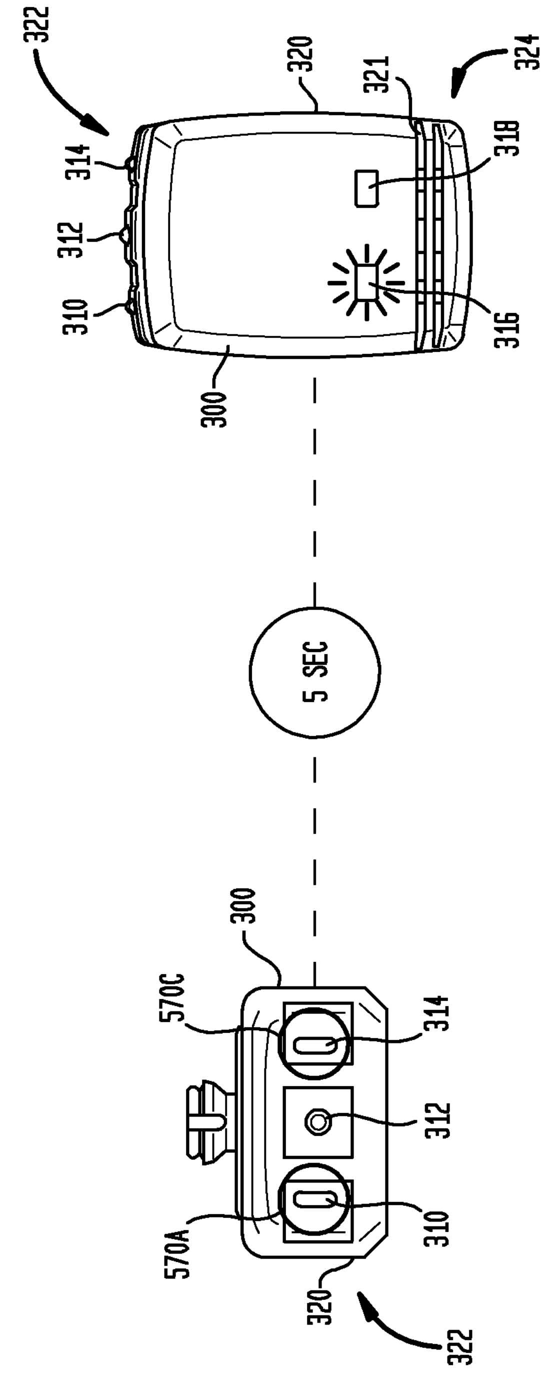
FIG. 5K is a top and side view of a bone conduction device, in accordance with embodiments of the present invention.

As shown in FIG. 5K, to enter the key lock mode, the recipient simultaneously presses buttons 310 and 314 for five seconds. After the five seconds have elapsed, the buttons of the bone conduction device will be locked, and, as such, pressing buttons 310, 312 and 314 will have no effect. Once the keys are locked, visual indicator 316 will flash three short flashes.

Figure 5L:
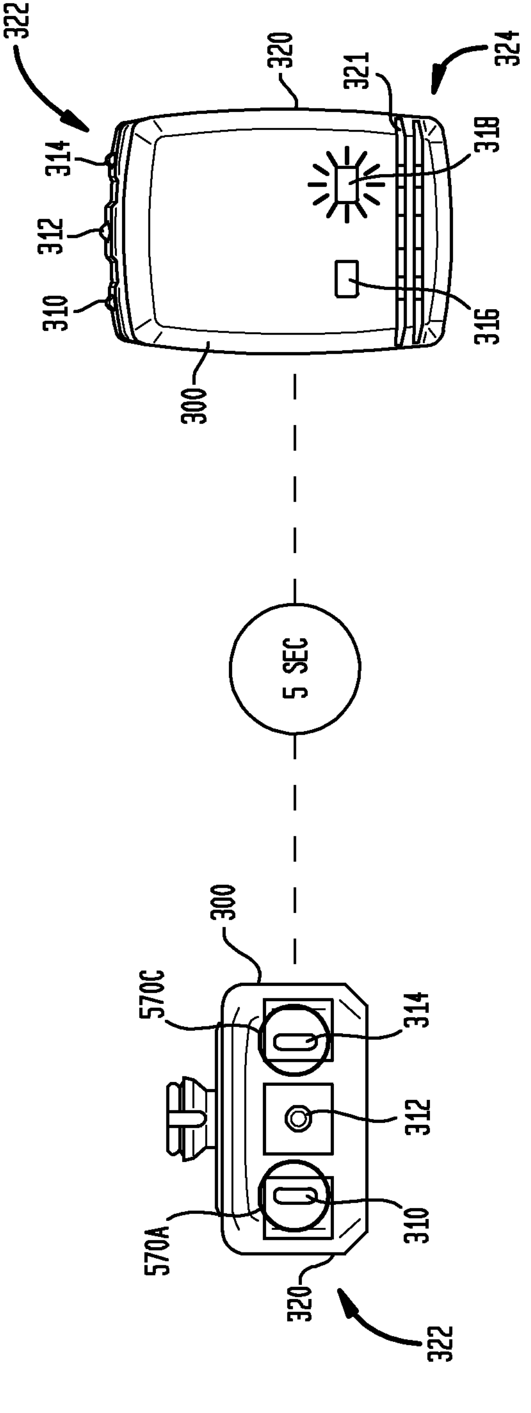
FIG. 5L is a top and side view of a bone conduction device, in accordance with embodiments of the present invention.

As shown in FIG. 5L, to exit the key lock mode, the recipient again simultaneously presses buttons 310 and 314 for five seconds. Once the buttons are unlocked, visual indicator 318 will flash three short flashes.

Embodiments of the present invention have been described with reference to a bone conduction device. However, embodiments may be practiced with other hearing prostheses such as electrically stimulating prostheses, such as cochlear implants or auditory brain implants, mechanical stimulators, acoustic hearing aids, etc.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A hearing prosthesis comprising:

an external component comprising:

a physically integrated input interface comprising:

an operational control interface having one or more interface elements;

a fitting control interface having one or more interface elements, wherein at least one of the fitting control interface elements comprises an operational control interface element;

a sound processor configured to process received sounds based on predefined fitting data; and an on-board fitting system configured to set the fitting data in response to control inputs received via the fitting control interface.

2. The hearing prosthesis of claim 1, wherein the prosthesis is configured to operate in a sound processing mode and a fitting mode, and wherein the fitting control interface is configured to receive user selections of real-time operation parameters of the hearing prosthesis when the hearing prosthesis is in the sound processing mode, and wherein the operational control interface is configured to receive selections of fitting data when the hearing prosthesis is in the fitting mode.

3. The hearing prosthesis of claim 2, wherein the operational control interface permits a user to set a volume level of the hearing prosthesis when in the sound processing mode.

4. The hearing prosthesis of claim 1, further comprising an output interface.

5. The hearing prosthesis of claim 4, wherein the fitting control interface comprises a manual interface having one or more manually operable interface elements.

6. The hearing prosthesis of claim 5, wherein the one or more manually operable interface elements comprise at least one of a pushbutton, a scroll wheel, a dial, a touch screen, a pressure sensor, a heat sensor, slide pad or switch.

7. The hearing prosthesis of claim 4, wherein the fitting control interface comprises a sound recognition system.

8. The hearing prosthesis of claim 4, wherein the output interface comprises at least one of a visual, audio, tactile and a stimulation indicator.

9. The hearing prosthesis of claim 8, wherein the output interface comprises at least one visual indicator, and wherein the visual indicator comprise at least one of an LED and an LCD.

10. The hearing prosthesis of claim 1, wherein the external component is configured to be worn on the side of a recipients head, and wherein the external component comprises a first microphone that faces substantially forward when the device is worn by the recipient, and a second microphone that faces substantially backward when the device is worn by the recipient.

11. The hearing prosthesis of claim 10, wherein the on-board fitting system is configured to set the directionality of the first and second microphones in response to control inputs received via the fitting control interface.

12. The hearing prosthesis of claim 1, wherein the on-board fitting system is configured to set at least one of a side fitting data parameter, a gain curve fitting data parameter, a functionality switch parameter, a low cut fitting parameter.

13. The hearing prosthesis of claim 1, wherein the hearing prosthesis is a bone conduction device.

14. The hearing prosthesis according to claim 1, wherein the hearing prosthesis is at least one of a cochlear implant, hearing aid, middle ear implant, and a hybrid device.

15. A hearing prosthesis configured to operate in a sound processing mode and a fitting mode comprising:

an external component having an integrated user interface configured to receive user selections of real-time operational parameters of the hearing prosthesis when the hearing prosthesis is in the sound processing mode, and wherein the user interface is configured to receive selections of fitting data when the hearing prosthesis is in the fitting mode;

a sound processor configured to process received sounds based on predefined fitting data; and an on-board fitting system configured to set the fitting data in response to control inputs received via the integrated user interface.

16. The hearing prosthesis of claim 15, wherein the integrated user interface comprises a physically integrated input interface and an output interface.

17. The hearing prosthesis of claim 16, wherein the integrated input interface comprises an operational control interface and a fitting interface, each having one or more interface elements.

18. The hearing prosthesis of claim 17, wherein the fitting control interface comprises one or more manually operable interface elements.

19. The hearing prosthesis of claim 17, wherein the fitting control interface comprises a sound recognition system.

20. The hearing prosthesis of claim 15, wherein at least one of the fitting control interface elements comprises an operational control interface element.

* * * * *